US008484812B2

(12) United States Patent
Meharry et al.

(10) Patent No.: US 8,484,812 B2
(45) Date of Patent: Jul. 16, 2013

(54) DENTAL CAST STABILIZER

(76) Inventors: Michael Robert Meharry, Moreno Valley, CA (US); Branden DaVault, Redlands, CA (US)

(*) Notice: Subject to any disclaimer, the term of this patent is extended or adjusted under 35 U.S.C. 154(b) by 185 days.

(21) Appl. No.: 13/188,725

(22) Filed: Jul. 22, 2011

(65) Prior Publication Data

US 2013/0022938 A1    Jan. 24, 2013

(51) Int. Cl.
*A61C 11/08*    (2006.01)
(52) U.S. Cl.
USPC .................. 24/484; 24/16 R; 433/60
(58) Field of Classification Search
USPC ............... 24/16 R, 16 PB, 17 A, 17 B, 17 AP, 24/30.5 P, 298, 300–302, 481, 482, 484; 433/60, 433/54, 49, 213
See application file for complete search history.

(56) References Cited

U.S. PATENT DOCUMENTS

| 2,373,328 | A | * | 4/1945 | Morehouse | 248/61 |
| 3,882,602 | A | * | 5/1975 | Polanco | 433/49 |
| 3,938,252 | A | * | 2/1976 | Polanco | 433/54 |
| 4,371,338 | A | * | 2/1983 | Mercer et al. | 433/60 |

* cited by examiner

*Primary Examiner* — James Brittain
(74) *Attorney, Agent, or Firm* — Michael R Meharry; Branden J. DaVault

(57) ABSTRACT

A dental cast stabilizer secures a dental cast to a dental cast articulator, and includes a fastening hole strap and a fastening post strap with a band body disposed therebetween. The fastening post strap includes a fastening post disposed thereon, and the fastening hole strap includes a fastening hole disposed thereon that is capable of receiving the fastening post or mounting plate thumb screw on an articulator.

9 Claims, 2 Drawing Sheets

DENTAL CAST STABILIZER

BACKGROUND OF THE INVENTION

The present invention generally relates to apparatus and methods for dental devices used in a dental laboratory, and, more particularly, to dental devices for mounting dental casts to dental articulators.

Some dental devices for mounting dental casts to dental articulators may require that the upper and lower portions of the dental cast be cemented or rigidly affixed together. Other dental devices for mounting dental casts may use plastic stick-like elements, a combination of wood sticks (including tooth picks) and dental waxes, or cements to stabilize dental casts for the mounting procedure. The use of the above described devices requires additional items for the procedure such as adhesives including cyanoacrylate cements (e.g., super glue), which can be toxic and adhere to human skin and are difficult to clean up if excess is used. The use of dental waxes (e.g., sticky wax) in some dental devices requires a heating device such as a torch or a flame to apply the wax, which may have its own inherent challenges and dangers of fire or burns.

As can be seen, there is a need for an improved apparatus and method that does not require a use of toxic glues or sticky substances and does not require an external heat source.

SUMMARY OF THE INVENTION

In one aspect of the present invention, a dental cast stabilizer for stabilizing a dental cast to a dental articulator comprises a fastening post strap, wherein a fastening post is disposed on the fastening post strap; a fastening hole strap, wherein a fastening hole is disposed on the fastening hole strap, and wherein the fastening post is configured to engage the fastening hole; and a band body having a first end and a second end, the first end connected to the fastening post strap, and the second end connected to the fastening hole strap.

In another aspect of the present invention, a dental cast stabilizer for securing a dental cast to a dental articulator comprises a maxillary mold and a mandibular mold, the dental articulator comprising an articulator upper arm and a mounting plate thumb screw, the dental cast stabilizer comprising a fastening post strap; a fastening hole strap for assembling to the fastening post strap or to engage the mounting plate thumb screw; a fastening hole disposed on the fastening hole strap and configured to engage the mounting plate thumb screw; a plurality of band bodies, each of the plurality of band bodies having a first end and a second end thereof, each of the first ends of the plurality of band bodies connected to the fastening post strap, and each of the second ends of the plurality of band bodies connected to the fastening hole strap, wherein the plurality of band bodies are configured to secure the dental cast in place; and a band waist that joins each of the plurality of band bodies.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a dental device for mounting dental molds to a dental articulator. Exemplary embodiments of the dental device do not require a use of toxic glues, sticky wax, or an external heat source, and allow the dental cast to be manipulated with or without occlusal registration.

Figure 1:
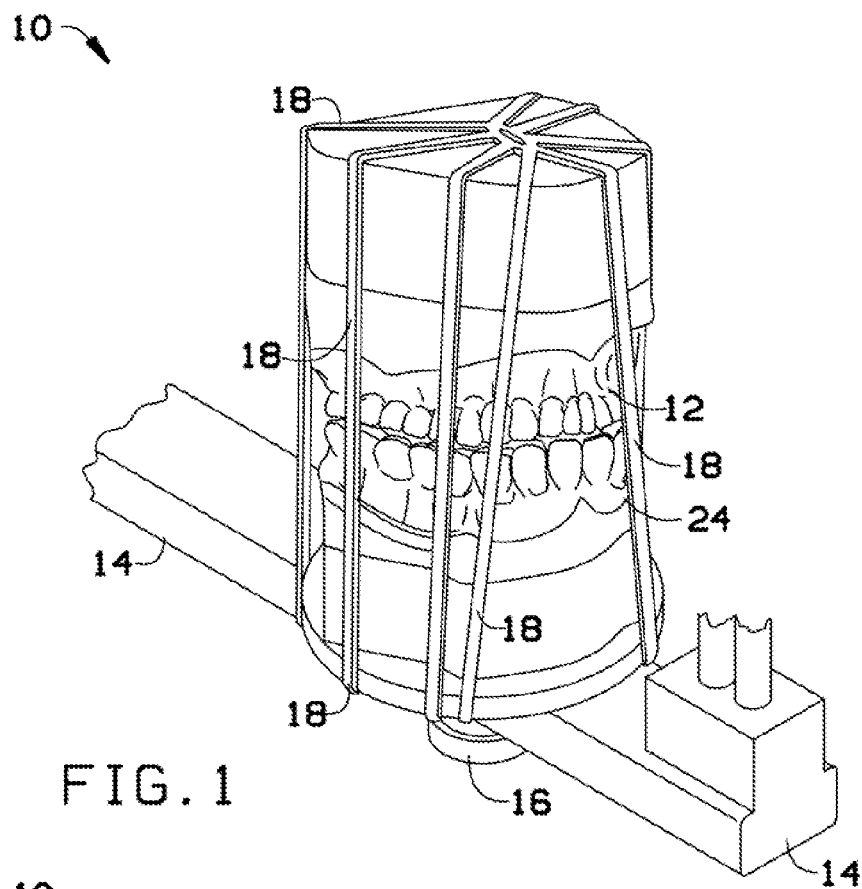
FIG. 1 is a an oblique perspective view of a dental cast stabilizer device in use on a dental articulator upper arm.
Figure 3:
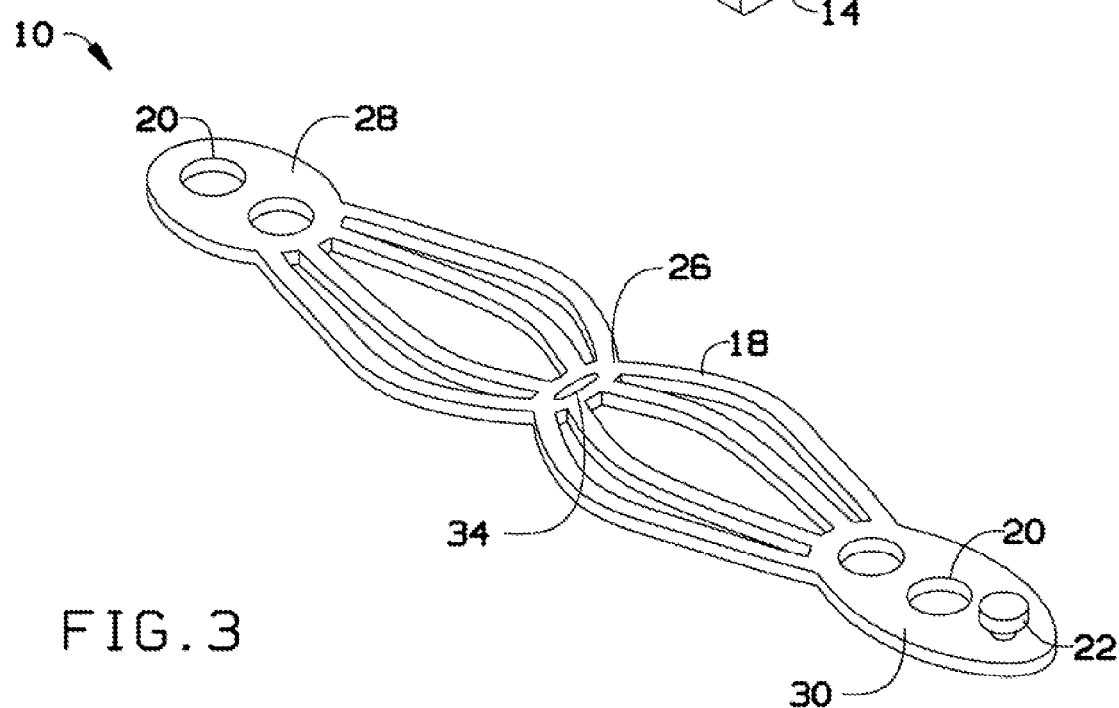
FIG. 3 is an oblique perspective view of the dental cast stabilizer device of FIG. 1.
Figure 4:
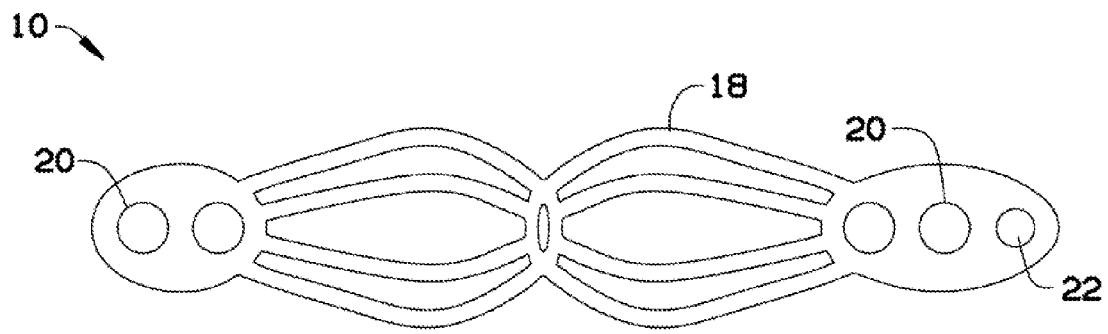
FIG. 4 is a top plan view of the dental cast stabilizer device of FIG. 1.
Figure 5:
FIG. 5 is a side perspective view of the dental cast stabilizer device of FIG. 1.
Figure 6:
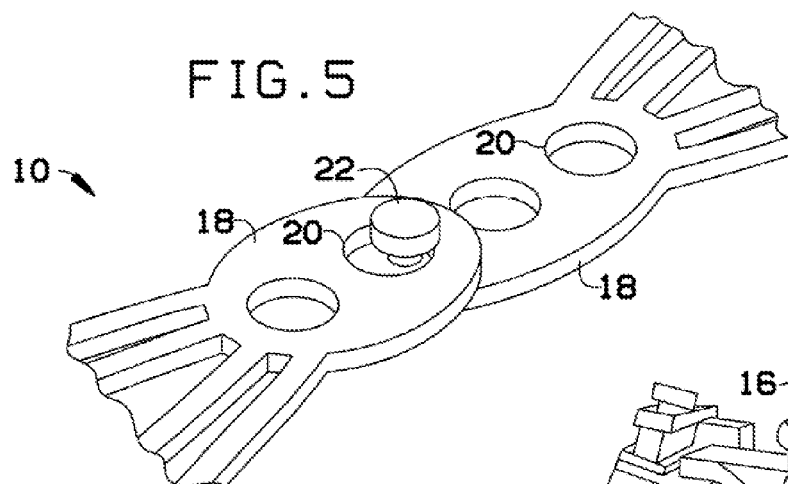
FIG. 6 is a detail view of the assembly of the dental cast stabilizer device of FIG. 1.
Figure 2:
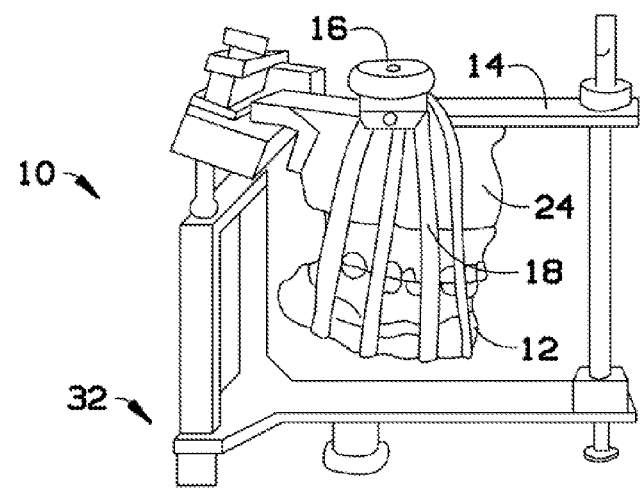
FIG. 2 is a side perspective view of the dental cast stabilizer device of FIG. 1 in use on a dental articulator.

Referring to FIGS. 1 and 2, a dental cast stabilizer device 10 is shown in use on a dental articulator 32. Dental articulator 32, which includes an articulator upper arm 14, may have a dental cast secured thereto. Dental casts include a mandibular cast 12 and a maxillary cast 24. A mounting plate thumb screw 16 may engage or secure device 10.

Referring to FIGS. 3-6, a band body 18 may have a fastening hole strap 28 connected to a first end thereof. Band body 18 may have a fastening post strap 30 connected to a second end thereof, opposite fastening hole strap 28. Band body 18 may include individual band bodies (e.g., first, second, third, and fourth band body) collectively referred to as band body 18 or as a plurality of band bodies. Band body 18 may have a band waist 26 that may join the plurality of band bodies along a length thereof. Fastening hole strap 28 and fastening post strap 30 may have fastening holes 20 formed or machined therein. Band waist 26 may have a fastening anchor 34 formed or machined therein Fastening hole strap 28 may have a plurality of fastening holes 20 formed therein along a length of device 10, and fastening post strap 30 may have a plurality of fastening holes 20 formed therein along a length of device 10.

Band body 18 may be elastic in at least one dimension, allowing device 10 to deform along a length thereof in response to a tensile force, for example. Fastening post 22 may include a stem 23a with a button 23b thereon. Fastening hole 20 may be a hole or slot that may be cut, formed, machined, stamped, or punched in device 10, and may be configured to engage fastening post 22 by an interference fit, for example. According to some exemplary embodiments, fastening post strap 30 and fastening hole strap 28 may include any complementary fastening components that may securely assemble, including a snap, a hook and loop fastener, or an adhesive surface, for example.

According to some exemplary embodiments, fastening hole strap 28 may include a plurality of fastening holes 20 (e.g., at least a first and a second fastening hole 20).

According to some exemplary embodiments, band body 18 may be about ⅛ of an inch thick. Fastening post strap 30 and fastening hole strap 28 may be about 1 inch wide. Fastening hole 20 may be about ½ inch in diameter. Device 10 may be between about 7 and about 8 inches in length in a relaxed configuration (e.g., no tensile force applied thereto), and may be a rubber, latex, or other synthetic elastomer, for example.

Device 10 may be used for mounting dental casts with or without occlusal registrations. A method of using device 10 may include mounting a maxillary cast with a jig or facebow in a conventional manner. A mandibular cast may alternatively be mounted with a jig or cross-mounted in a conventional manner. The remaining cast may then be positioned and aligned with the mounted cast in either a maximum intercuspation position or with the occlusal registration. The dental cast may be held in place by placing a fastening hole 20 (e.g., located on fastening post strap 30 or fastening hole strap 28) or a fastening anchor 34 to an articulator mount fastener (e.g., mounting plate thumb screw 16). Device 10 may then be stretched under the cast, bringing device 10 along an opposite side of device 10, and fastening post 22 may be assembled to fastening hole 20 of fastening hole strap 28. A tension of device 10 and an occluding tightness of the casts may be adjusted by selecting one of two or more fastening holes 20 on fastening hole strap 28.

It should be understood, of course, that the foregoing relates to exemplary embodiments of the invention and that modifications may be made without departing from the spirit and scope of the invention as set forth in the following claims.

What is claimed is:

1. A dental cast stabilizer for stabilizing a dental cast to a dental articulator, the dental cast stabilizer comprising:
   a fastening post strap, wherein a fastening post is disposed on the fastening post strap;
   a fastening hole strap, wherein a fastening hole is disposed on the fastening hole strap, and wherein the fastening post is configured to engage the fastening hole; and
   a band body having a first end and a second end, the first end connected to the fastening post strap, and the second end connected to the fastening hole strap, further comprising:
   a second band body having a second band body first end and a second band body second end, the second band body first end connected to the fastening post strap, and the second band body second end connected to the fastening hole strap; and
   a band waist, wherein the band waist is configured to join the band body and the second band body at a point along lengths of the band body and the second band body.

2. The dental cast stabilizer of claim 1, further comprising: a third band body; and
   a fourth band body, wherein the band waist is configured to join the band body, the second band body, the third band body, and the fourth band body at points along lengths of the band body, the second band body, the third band body, and the fourth band body.

3. The dental cast stabilizer of claim 2, wherein the band waist is midway along a length of the band body, the second band body, the third band body, and the fourth band body.

4. The dental cast stabilizer of claim 3, wherein a fastening anchor is disposed on the band waist, wherein the fastening anchor is configured to assemble to an upper arm of the dental articulator.

5. The dental cast stabilizer of claim 4, further comprising a second fastening hole disposed on the fastening hole strap, wherein the fastening post is configured to engage the second fastening hole.

6. The dental cast stabilizer of claim 5, further comprising a third fastening hole disposed on the fastening post strap.

7. A dental cast stabilizer for securing a dental cast to a dental articulator, the dental cast comprising a maxillary mold and a mandibular mold, the dental articulator comprising an articulator upper arm and a mounting plate thumb screw, the dental cast stabilizer comprising:
   a fastening post strap;
   a fastening hole strap for assembling to the fastening post strap or to engage the mounting plate thumb screw;
   a first fastening hole disposed on the fastening hole strap and configured to engage the mounting plate thumb screw;
   a plurality of band bodies, each of the plurality of band bodies having a first end and a second end thereof, each of the first ends of the plurality of band bodies connected to the fastening post strap, and each of the second ends of the plurality of band bodies connected to the fastening hole strap, wherein the plurality of band bodies are configured to secure the dental cast in place;
   and a band waist that joins each of the plurality of band bodies.

8. The dental cast stabilizer of claim 7, wherein the fastening post strap includes a fastening post.

9. The dental cast stabilizer of claim 8, further comprising a second fastening hole adjacent to the first fastening hole disposed on the fastening hole strap, wherein the second fastening hole is also configured to engage the mounting plate thumb screw, and wherein the fastening post engages either fastening hole by an interference fit.

* * * * *